United States Patent
Huang

(10) Patent No.: US 9,592,156 B2
(45) Date of Patent: Mar. 14, 2017

(54) LASER BEAM OPHTHALMOLOGICAL SURGERY METHOD AND APPARATUS

(71) Applicant: Cheng-Hao Huang, Orlando, FL (US)

(72) Inventor: Cheng-Hao Huang, Orlando, FL (US)

(73) Assignee: Excelsius Medical Co. Ltd., Tainan (TW)

(*) Notice: Subject to any disclaimer, the term of this patent is extended or adjusted under 35 U.S.C. 154(b) by 569 days.

(21) Appl. No.: 14/061,123

(22) Filed: Oct. 23, 2013

(65) Prior Publication Data

US 2014/0046306 A1    Feb. 13, 2014

Related U.S. Application Data

(63) Continuation-in-part of application No. 13/404,127, filed on Feb. 24, 2012, now abandoned.

(51) Int. Cl.
*A61F 9/008* (2006.01)

(52) U.S. Cl.
CPC ...... *A61F 9/00804* (2013.01); *A61F 2009/00872* (2013.01); *A61F 2009/00897* (2013.01)

(58) Field of Classification Search
CPC ...... A61F 9/008; A61F 9/00804; A61B 18/20; A61B 3/107
USPC ............................................ 606/4, 5, 11, 16
See application file for complete search history.

(56) References Cited

U.S. PATENT DOCUMENTS

| | | | |
|---|---|---|---|
| 5,480,396 A | 1/1996 | Simon et al. | |
| 5,599,340 A | 2/1997 | Simon et al. | |
| 6,325,792 B1* | 12/2001 | Swinger | A61F 9/00804 606/11 |
| 2008/0039825 A1* | 2/2008 | Lai | A61B 3/107 606/5 |
| 2010/0049175 A1* | 2/2010 | Rathjen | A61F 9/008 606/5 |
| 2010/0100086 A1* | 4/2010 | Boutoussov | A61B 18/20 606/16 |
| 2010/0318073 A1* | 12/2010 | Vogler | A61F 9/008 606/4 |
| 2013/0131653 A1 | 5/2013 | Huang | |

* cited by examiner

*Primary Examiner* — William Thomson
*Assistant Examiner* — Victor Shapiro
(74) *Attorney, Agent, or Firm* — William M. Hobby, II

(57) ABSTRACT

This invention is related to refractive eye surgery and specifically regarding guiding a laser beam through free space using a set of rotatable mirrors to guide said laser beam into a hand piece module that converts the laser beam into a two dimensional random overlapping scanning parallel laser beam that is delivered to the eye for ablation of cornea tissue to reshape the cornea of the eye. The rotating mirror set module allows a hand piece having an eye stabilization and distance control unit to be positioned by the surgeon onto a patient's eye for performing the surgery.

10 Claims, 2 Drawing Sheets

LASER BEAM OPHTHALMOLOGICAL SURGERY METHOD AND APPARATUS

This patent application is a continuation-in-part application of my pending U.S. patent application Ser. No. 13/404,127, filed Feb. 24, 2012 for LASER BEAM OPHTHALMOLOGICAL SURGERY METHOD AND APPARATUS.

BACKGROUND OF THE INVENTION

This invention is related to refractive eye surgery and specifically regarding guiding a laser beam through free space using a set of rotatable mirrors into a hand piece module that converts the laser beam into a two dimensional random overlapping scanning parallel laser beam that is delivered to the eye for ablation of cornea tissue to reshape the cornea of the eye.

About three-quarter of the refractive power of the eye is determined by the curvature of the anterior surface of the cornea and changing the shape of the cornea offers a way to significantly reduce or eliminate refractive errors of the eye. The stroma is thick enough that portions of its anterior region can be ablated away to change its profile and thus change the refractive power of the eye for corrective purposes while leaving plenty of remaining stroma tissue.

Various lasers have been used for ophthalmic applications including the treatment of glaucoma, cataract and refractive surgery. For refractive surgery (or corneal reshaping), ultraviolet (UV) lasers, such as excimer lasers at 193 nm and fifth-harmonic Nd:YAG at 208-213 nm have been used for large area surface corneal ablation in a process called photorefractive keratectomy (PRK) and for large area stroma ablation in a process called laser assisted in situ keratomileusis (LASIK). Corneal reshaping may also be performed by laser thermal coagulation currently conducted with Ho:YAG laser using a fiber-coupled contact and flying laser spots non-contact type process.

Refractive surgery has reached an acceptable level of consistency and proficiency due to the development of the excimer laser and fifth harmonic solid state laser used to photo ablate the corneal tissue to reshape the cornea. In my prior U.S. Pat. No. 5,480,396 dated Jan. 2, 1996 for LASER BEAM OPHTHALMOLOGICAL SURGERY METHOD AND APPARATUS and U.S. Pat. No. 5,599,340 dated Feb. 4, 1997 for LASER BEAM OPHTHALMOLOGICAL SURGERY METHOD AND APPARATUS, single or plural beams are formed by splitting one laser beam, and using a random scanning pattern of the beams to scan the laser beams over the cornea. Most of the current commercial refractive laser systems use either one or two laser beams and a random scanning pattern.

However, all the refractive laser systems currently available in the market are similar in that they require the patient's eye to align with a fixed delivery laser beam. In this case, the laser cabinet is bulky and a fixed laser delivery arm is used to transfer the laser beam into a random scanning pattern onto the cornea. The laser delivery arm is around one meter in length and the laser beam is turned down under the microscope in order to align the laser beam with the microscope's visual axis. The distance from the lower part of the laser delivery arm to the surface of the cornea is around 250 millimeters. The patient lies down on a table that can be XYZ fine-tuned in order to move the patient's eye to the focusing point of the microscope and laser delivery set up. Using this arrangement, the patient is required to move in order to align the patient's eye to the laser beam. To prevent eye movement during the surgery, the surgeon uses a ring or other tools to stabilize the eye ball. Most of the modern laser systems employ an eye tracker system to follow eye movement but even the most advanced three dimensional eye tracking system cannot guide the laser beam to normal incidence upon the corneal surface due to the rotational nature of the eye ball.

U.S. Pat. No. 5,599,340 describes an UV laser with an XY scanned device that delivers the laser beam from a fixed point to the cornea without any physical contact with eye. The visual axis of a microscope is aligned with the UV laser beam since the microscope is used to monitor the ablation. A sophisticated movement patient table is used to move the patient's eye into alignment with the visual axis of the microscope and the UV laser beam. This requires significant effort for the surgeon to precisely align the beam with the eye.

U.S. Patent Application Publication No. US 2013/0131653 A1 (EMI femtosecond laser application) consists of a femtosecond laser apparatus where the laser beam pulses are sent through an XY-scanning device located in a main cabinet. The beam then travels through a mirror-lens relay optical arm to a hand piece that contains a XYZ piezo stage and a very short focal length lens with a high numerical aperture. The hand piece is connected to the surface of the eye via a suction ring. This apparatus therefore aligns the laser beam with the eye to simplify the surgical procedure by removing the process of aligning the patient using a sophisticated movement patient table to align the eye with the laser beam.

However, the function of a femtosecond laser apparatus in refractive surgery is to cut and create a flap in the cornea whereas the function of a UV laser or fifth-harmonic Nd:YAG system in refractive surgery is to ablate and reshape the cornea. Due to the difference in the nature of the procedure between the two type of systems, a millimeter sized laser spot and a 10 mm ablation area is required for UV (excimer or fifth-harmolic solid state) laser refractive surgery whereas the femtosecond apparatus utilize a significantly smaller 2-5 micron laser spot size and an ablation area less than 10 mm. A key difference to the femtosecond laser is an UV laser's sensitivity to laser loss as its laser path increases. This attribute makes it preferable in current UV laser apparatus designs to deliver the laser source via a fixed arm to shorten the laser path. To compensate for eye movement, all current market leaders utilize an eye tracker to account for the fixed arm delivery's sensitivity to eye movement. A flexible articulated mirror arm lengthens and complicates the UV laser's path and is not an obvious solution to current refractive surgery problems.

The present invention proposes a design for a laser system in which the laser beam aligns with the patient's eye rather than having the patient's eye aligned to a fixed UV laser beam delivery point. The laser system uses a rotatable mirror set module to transfer the laser beam from the laser source into a hand piece module at its normal entrance plane without the use of any lenses along the path. In order to overcome the long UV laser path loss and alignment sensitivity, the present invention uses only mirrors in an optical arm as opposed to mirrors and lenses (mirror-lens relay optical arm). Placing lenses in an optical arm amplifies alignment errors and creates a more complex module. Therefore, the present invention uses a mirror set module containing only mirrors to transmit the light source to simplify the optical system's design and operation. Also, a purged nitrogen gas design is incorporated in the laser beam path to reduce the UV laser traveling loss through air. The hand piece module, which contains a two dimensional scanner (such as a piezo tip/tilt scanner or a set of galvanometer scanners), a f-theta telecentric scan focusing lens and other surgery aiding designs/devices converts the laser beam to a two dimensional parallel scanning laser beam as it exits the hand piece and onto the patient's eye. The f-theta telecentric scan focusing lens both focuses the laser beam and converts it from divergent scanning to parallel scanning. The parallel scanning characteristic improves ablation efficiency along the peripheral of the cornea. In the new system, even if the eye is moving during the surgery, the laser beam remains at normal incidence on the eye due to it's flexible nature. Eye trackers in current systems cannot accomplish this and are unnecessary in our invention.

SUMMARY OF THE INVENTION

A laser ophthalmological surgery apparatus uses a method of ablating eye tissue which includes generating a UV laser beam, such as an excimer laser, and directing the generated laser beam through a manually activated shutter, a homogenizer and a rotating mirror set module so the laser beam enters the hand piece module at normal incidence to its entrance plane. In the hand piece module, the laser beam passes through a two dimensional scanner (piezo tip/tilt scanner or galvanometer set) and is converted to a two dimensional random overlapping scanning diverging laser beam. A computer generates the random scanning pattern signal, for controlling the scanner to produce the two dimensional random overlapping scanning pattern from the input laser beam. The laser beam then passes through an f-theta telecentric scan focusing lens to convert the laser beam into a two dimensional overlapping randomly scanned parallel laser beam. A dielectric mirror deflects the laser beam as it exits the hand piece module and onto the patient's eye. The hand piece module has an eye stabilization and distance control unit with an open center area used to align the eye to the hand piece via direct contact. The selected hand piece also has at least one or more (typically four) near infrared illumination lights mounted on the hand piece for aligning the eye stabilization and distance control member to a patient's eye and a video camera attached to facilitate surgery observation. The generated laser beam exits the hand piece module through the open center of the eye stabilization and distance control member. The hand piece module is connected to the end of the rotating mirror set module and moved to align the eye stabilization and distance control unit into contact with a patient's eye. The hand piece is aligned utilizing a microscope. There is an alignment hole above the dielectric mirror that allows the user to center the eye stabilization and distance control member on the patient's pupil using the microscope through the alignment hole. A visible light beam directed through the microscope and alignment hole is used to guide the patient's eye focus at normal incidence to the hand piece. There is a hot mirror placed above the dielectric mirror under the alignment hole to guide the near infrared reflecting light to the video camera and enhance image quality and processing capability by reducing visible light noise for the video camera. The laser beam is then impinged onto the surface of the patient's eye responsive to activation of the shutter to ablate tissue from the surface of the patient's eye. Thus surgical ablation is performed on a patient's eye with a two dimensional overlapping randomly scanned parallel laser beam through a hand manipulated hand piece in contact with the patient's eye.

A rotating mirror set module has a hand piece module attached to one end and the other end positioned for receiving the laser beam and directing the laser beam to the hand piece module and through an open center area of the eye stabilization and distance control member. The rotating mirror set module has multiple rotatable mirrors that work in conjunction and manipulates the direction of the laser beam so that it enters the hand piece at normal incidence. The hand piece can be positioned to direct the laser beam onto a patient's eye by manipulating the rotating mirror set module. A vacuum pump has a vacuum line connected to the hand piece to remove the eye's ablated tissue. Surgical ablation can thus be performed on a patient's eye with a two dimensional random overlapping parallel scanning laser beam through a hand manipulated hand piece in contact with the patient's eye.

BRIEF DESCRIPTION OF THE DRAWINGS

The accompanying drawings, which are included to provide further understanding of the invention and are incorporated in and constitute a part of the specification, illustrate an embodiment of the invention and together with the description serve to explain the principles of the invention. In the drawings.

DETAILED DESCRIPTION OF EXEMPLARY EMBODIMENT

Figure 1:
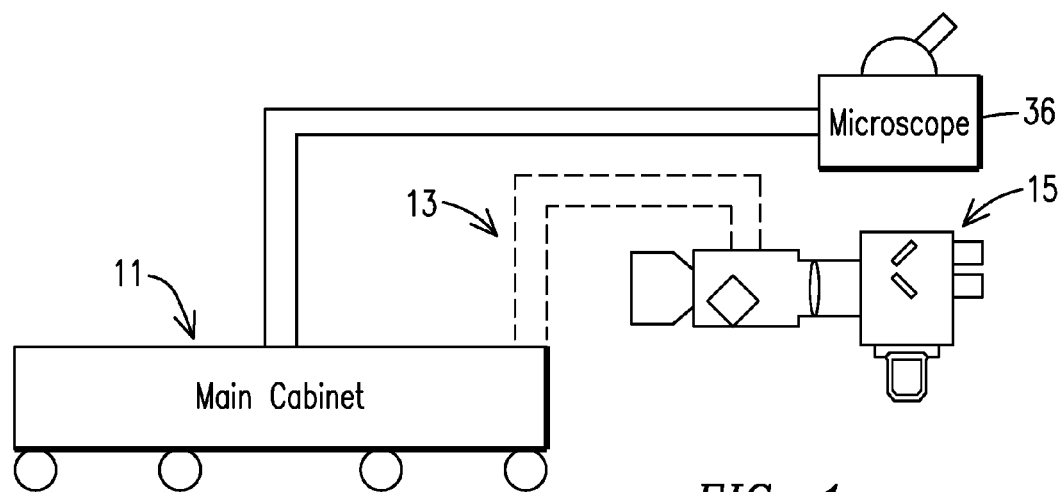
FIG. 1 is a drawing of the exterior of the critical modules of the apparatus and how they fit together to form the laser ophthalmological surgery apparatus.
Figure 2:
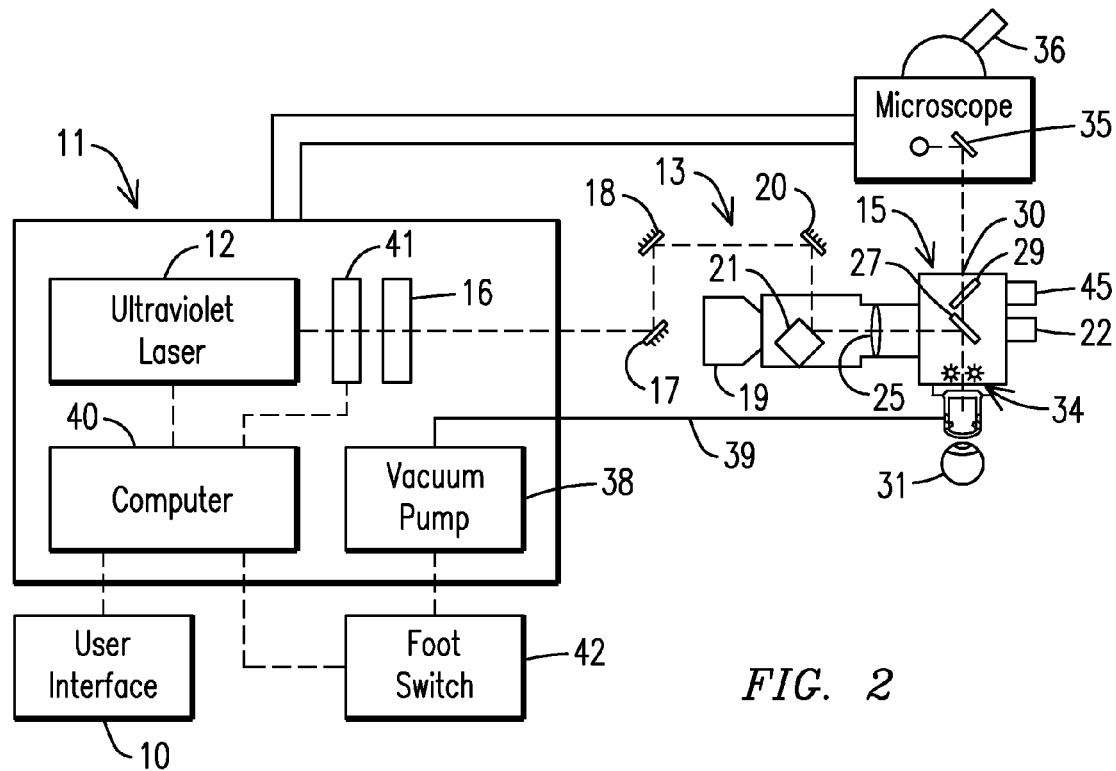
FIG. 2 is a block diagram of an ophthalmologic laser surgery apparatus in accordance with the present invention.

The laser ophthalmological surgery apparatus in accordance with the present invention as seen in the drawings, FIGS. 1 through 6, includes a user interface 10, in FIG. 2, connected to a main cabinet 11. Within the main cabinet, laser pulses are generated with UV laser 12 that is guided through an attached rotating mirror set module 13. The ophthalmological apparatus has a main cabinet and a hand piece module 15 connected to either end of the rotating mirror set module. The UV laser is positioned in the main cabinet 11 and has a laser beam output of laser pulses. A laser beam homogenizer 16 is positioned to homogenize the laser beam to smooth out irregularities in the laser beam before it is directed through the rotating mirror set module.

Figure 4:
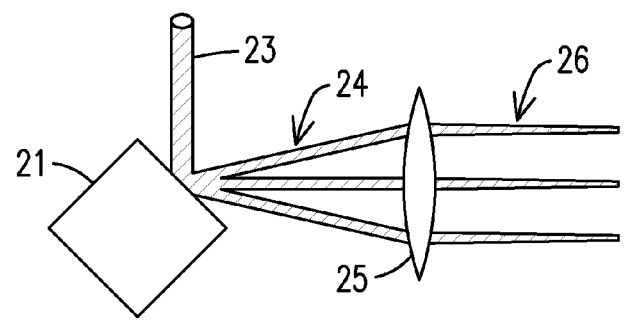
FIG. 4 is a side diagrammatic view of the hand piece of FIGS. 1 and 2 showing the change in UV laser characteristic as it exits the mirror set module, deflects from the two dimensional scanner (becomes divergent scanning) and then bypasses the f-theta telecentric scan focusing lens (becomes parallel scanning)
Figure 3:
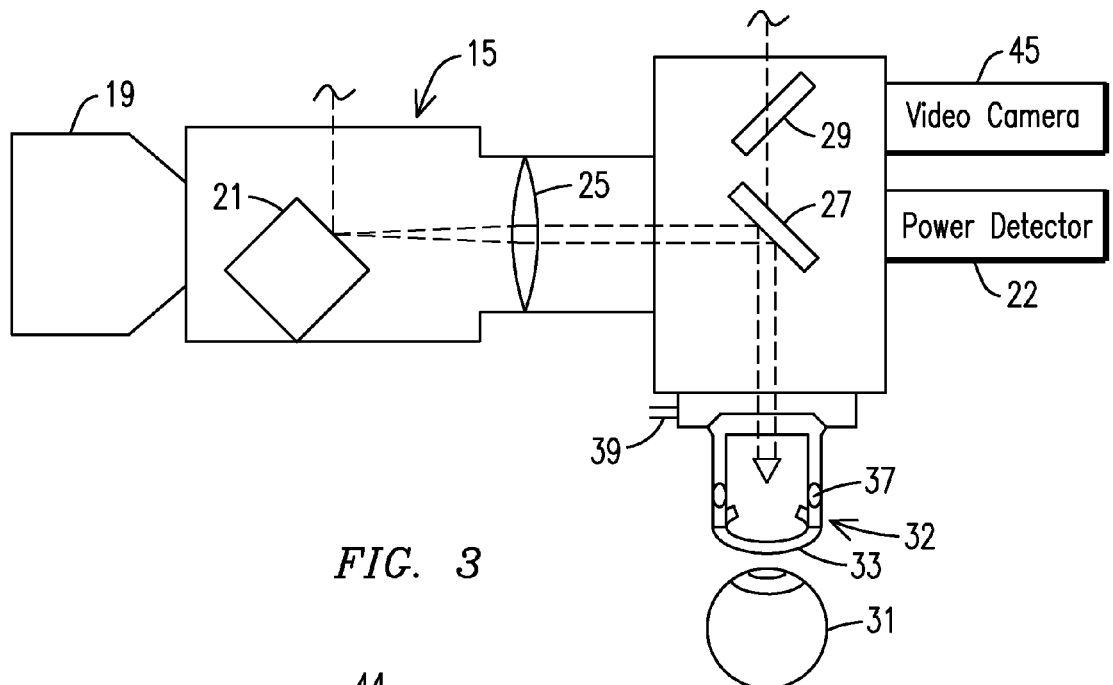
FIG. 3 is a side diagrammatic view of the hand piece of FIGS. 1 and 2 positioned on a patient's eye.

A method of ablating eye tissue, as illustrated in FIGS. 2 through 4, generates a pulse laser beam from an UV laser 12. The laser beam passes through the rotating mirror set module 13 having mirrors 17, 18, 20 (for demonstration; can have more than three mirrors) and into the hand piece module 15 at normal incidence to the two dimensional scanner 21 where it has the same characteristics and properties as the output from the UV laser 12. The hand piece 15 is counterweighted with weight 19. A power detector or meter 22 is used to monitor the power level of the laser beam.

As seen in FIG. 4, the laser beam 23 first passes through the two dimensional scanner 21 in the hand piece module 15 and becomes a two dimensional random overlapping scanning diverging laser beam 24. The laser beam 24 then passes through a f-theta telecentric scan focusing lens 25 which focuses and converts the laser beam to a parallel scanning laser beam 26. Finally, the laser beam is guided by 45 degree reflecting turn down dielectric mirror 27, in FIG. 3, to direct the laser beam out of the hand piece 15.

Using the microscope 36, in FIGS. 2 and 3, through the alignment hole 30 and hot mirror 29, the hand piece 15 is then aligned in contact with the eye 31 via the eye stabilization and distance control unit 32 eye contact surface 33 which levels the focused laser beam spot onto the eye and stabilizes the eye. Four near infrared centering lights 34 are used to position the hand piece eye stabilization and distance control unit 32 onto the eye. One visible light beam source 35 is placed in the microscope 36 and used to attract the patient's eye focus to align the patient eye's visual axis coincidence with the microscope's visual axis. The laser beam exits the hand piece 15 onto a patient's eye to ablate a predetermined pattern of eye tissue in the patient's eye. The patient's eye is thus ablated in a predetermined overlapping random scanning pattern with a controlled focused laser beam of an UV laser 12.

Two tissue debris suction tubes 39 are attached on the eye stabilization and distance control unit to remove the laser ablation particles through suction vents 37 to avoid the interference of tissue particles and is connected to a vacuum pump 38. A user interface is connected to a computer 40 which in turn is used to control the vacuum pump 38 and the shutter 41 as well as the two dimensional scanner 21. The shutter 41 opens and closes to control the laser pulses that are applied through the homogenizer 16 and to the scanner 21.

Following the light path in greater detail, the UV light pulse generator is an excimer laser (wavelength 193 nm) or fifth harmonic generated solid state laser (wavelength is from 193 nm to 213 nm) with a pulse width less than 20 nanosecond and a pulse repetition rate from 100 Hz to several thousand Hz. The laser beam is blocked by the shutter 41 until the foot switch 42 is depressed thereby activating a switch. While the foot switch 42 is pressed, the laser beam is allowed to continue to the homogenizer 16 where the laser beam spot size is homogenized, i.e. smooths out the irregularities in the laser beam. The beam continues into the rotating mirror set module 13. The purpose of the mirrors 17, 18, and 20 is so the laser beam enters the hand piece module 15 with the same characteristics and properties as the output from the laser source and is aligned at normal incidence to the two dimensional scanner 21.

Figure 5:
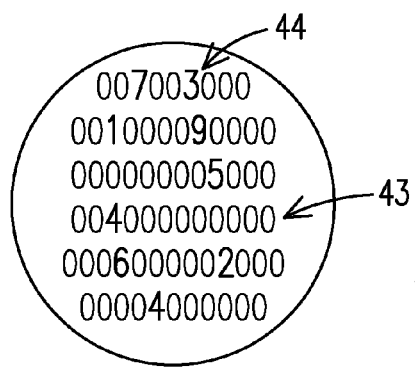
FIG. 5 shows a randomized scanning pattern where the numbers are in the order in which the first nine laser beam spots are scanned. While the laser spots overlap, the spots shown in this figure are non-overlapping for the sake of clarity.
Figure 6:
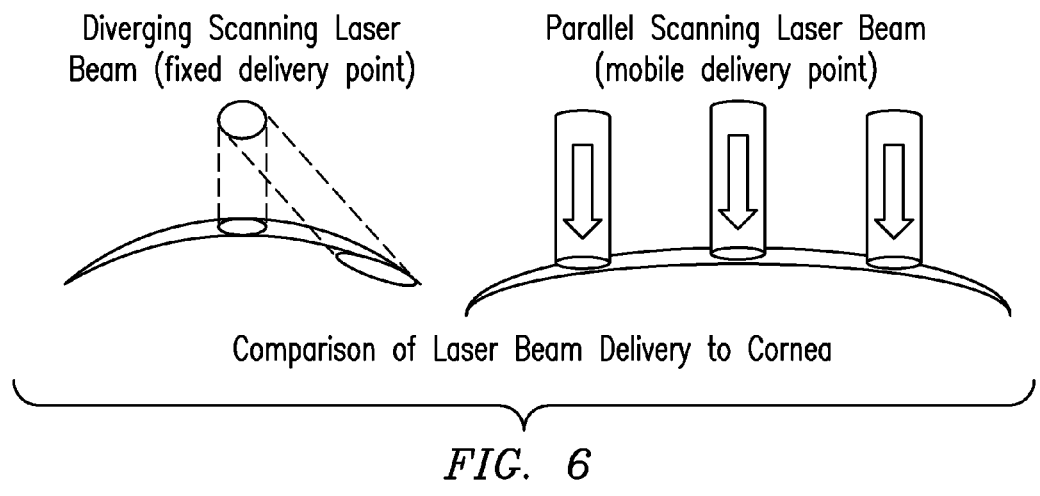
FIG. 6 is a drawing demonstrating the difference between ablation efficiency between a fixed point divergent scanning and a parallel scanning laser beam. Parallel scanning allows the laser beam to make contact with the periphery of the cornea at closer to normal incidence compared to fixed point divergent scanning laser beam.

Inside the hand piece module 15, a f-theta telecentric scan focusing lens 25 is used to reduce the spot size of the laser beam spots 44 to approximately 1 mm and the size of the overlapping random scanning pattern 43 to a diameter of less than 10 mm as seen in FIG. 5. A f-theta telecentric scan focusing lens 25 also converts the laser beam from diverging to parallel scanning as seen in the comparison in FIG. 6. The turn down dielectric mirror 27 (FIG. 2) directs the laser beam towards the eye 31 while a power meter 22 detects the laser beam's power.

The eye 31 will have some minor movements during surgery. However, the laser beam is always maintained at a normal incidence to the eye since the hand piece 15 is in contact and can rotate with eye movement. The four near infrared centering lights 34 are used to delineate the target area. A visible light beam built into the microscope 36 directs the view of the eye through the hot mirror 29 and into alignment with the hand piece 15. The eye 31 is illuminated by the four near infrared centering lights 34 and is viewable through a video camera 45 so that the system's computer 40 can receive the video signal to detect the pupil location to provide feedback during the centering procedure.

The ablation patterns as seen in FIG. 5 are generated by the laser 12 and includes but is not limited to predetermined myopia, hyperopia and astigmatism patterns. The computer 40 randomly rearranges the ordered ablation data into a new random sequence of ablation. The laser beam spots are delivered to the cornea in overlapping random patterns.

It should be clear at this time that a process and an apparatus for performing refractive eye surgery by surgical ablation on a patient's eye has been shown which guides a UV laser beam through a rotating mirror set module and delivers a two dimensional random overlapping parallel laser beam through a hand manipulated hand piece in contact with the patient's eye. However the present invention is not to be considered limited to the forms shown which is to be considered illustrative rather than restrictive.

I claim:
1. A method of ablating eye tissue comprising the steps of:
selecting a laser ophthalmological surgery apparatus having a UV laser for generating a laser beam and having a hand piece having a scanner and an f-theta telecentric scan focusing lens therein to convert the laser beam from a divergent to a parallel scanning laser beam, said hand piece having an eye stabilization and distance control unit extending therefrom having an open center area and an eye contact edge thereon, said hand piece having an aligning light thereon for aligning the eye stabilization and distance control unit with a patient's eye, said apparatus having a rotatable mirror set module coupling said UV laser to said hand piece;
generating a UV laser beam having a wavelength from 193 nm to 213 nm with said UV laser;
generating an overlapping random scanning pattern laser beam control signal;
applying the generated UV laser beam through a rotating mirror set module into said selected hand piece;
directing the generated UV laser beam onto hand piece scanner;
applying the generated overlapping random scanning pattern laser beam control signal to said scanner to generate a two-dimensional overlapping random scanning diverging laser beam pattern;
applying the two-dimensional overlapping random scanning diverging laser beam through said f-theta telecentric scanning focusing lens mounted in said hand piece to convert the laser beam from a divergent scanning to parallel scanning laser beam;
manipulating said hand piece on said rotating mirror set module to align said eye stabilization and distance control unit on a patient's eye and to bring said eye stabilization and distance control unit into eye contact with a patient's eye;

directing said parallel scanning laser beam through the open center of said eye stabilization and distance control unit; and impinging said two-dimensional parallel overlapping random scanning laser beam from said hand piece onto the surface of the patient's eye to ablate tissue from the surface of the eye;

whereby surgical ablation is performed on a patient's eye with a two-dimensional overlapping random scanning parallel laser beam through a hand manipulated hand piece in contact with the patient's eye.

2. The method of ablating eye tissue in accordance with claim 1 in which said scanner is a two dimensional scanner.

3. The method of ablating eye tissue in accordance with claim 2 in which the selected hand piece has a video camera mounted thereon for recording the open center area in the eye stabilization and distance control member.

4. The method of ablating eye tissue in accordance with claim 3 in which said selected hand piece has a power meter thereon.

5. The method of ablating eye tissue in accordance with claim 4 in which said hand piece has aligning lights thereon.

6. The method of ablating eye tissue in accordance with claim 5 including the step of connecting a vacuum pump suction line to said hand piece to remove ablated eye tissue while surgically ablating a patient's eye.

7. The method of ablating eye tissue in accordance with claim 6 including the step of directing the generated laser beam through a homogenizer to smooth out irregularities in the laser beam prior to directing the laser beam onto the rotating mirror set module.

8. The method of ablating eye tissue in accordance with claim 7 including the step of directing the generated laser beam through a shutter prior to directing the laser beam through the homogenizer.

9. The method of ablating eye tissue in accordance with claim 8 including the step of computer controlling said laser to generate the laser beam, shutter and the two dimensional scanner responsive to a foot pedal switch during surgery on a patient's eye.

10. A laser ophthalmological surgery apparatus for ablating eye tissue comprising:

a UV laser for generating a laser beam;

a hand piece having a laser beam scanner and an f-theta telecentric scan focusing lens therein for converting the laser beam from a divergent to a parallel scanning laser beam, said hand piece having an eye stabilization and distance control unit therein and extending therefrom and said hand piece having an open center area and an eye contact edge thereon and said hand piece having an aligning light thereon for aligning the eye stabilization and distance control unit with a patient's eye; and a rotating mirror set module coupling said UV laser beam into said hand piece for directing said laser beam through said laser beam scanner and f-theta telecentric scan focusing lens in said hand piece and onto a patient's eye to surgically ablate the patient's eye with a parallel scanning laser beam;

whereby surgical ablation of a patient's eye can be performed with a two-dimensional overlapping random scanning parallel laser beam through a hand manipulated hand piece in contact with the patient's eye.

* * * * *